United States Patent [19]
Kumazawa

[11] Patent Number: 5,163,434
[45] Date of Patent: Nov. 17, 1992

[54] ULTRASONIC DIAGNOSTIC APPARATUS

[75] Inventor: Takashi Kumazawa, Ootawara, Japan

[73] Assignee: Kabushiki Kaisha Toshiba, Kawasaki, Japan

[21] Appl. No.: 585,235

[22] Filed: Sep. 20, 1990

[30] Foreign Application Priority Data

Sep. 20, 1989 [JP] Japan .................................. 1-244607

[51] Int. Cl.$^5$ ................................................ A61B 8/06
[52] U.S. Cl. .............................................. 128/661.09
[58] Field of Search ................... 128/661.08–661.10, 128/660.01; 73/861.25

[56] References Cited

U.S. PATENT DOCUMENTS

| | | | |
|---|---|---|---|
| 4,324,258 | 4/1982 | Huebscher et al. | 128/661.09 |
| 4,541,437 | 9/1985 | Amemiya | 128/661.09 |
| 4,593,700 | 6/1986 | Hayakawa et al. | 128/661.09 |
| 4,683,893 | 8/1987 | Mayo | 128/660.01 |
| 4,830,016 | 5/1989 | Tamano et al. | 128/661.09 |
| 4,850,364 | 7/1989 | Leavitt | 128/661.09 |

Primary Examiner—Francis Jaworski
Attorney, Agent, or Firm—Oblon, Spivak, McClelland, Maier & Neustadt

[57] ABSTRACT

An ultrasonic diagnostic apparatus includes an ultrasonic transmitting/receiving section for transmitting an ultrasonic wave into an object to be examined and receiving an ultrasonic echo of the transmitted ultrasonic wave, a detecting section for detecting a frequency shift component from an ultrasonic echo signal obtained by the ultrasonic transmitting/receiving section, a filter section for removing a clutter component from a detection signal obtained by the detecting section and extracting only a required Doppler shifted signal, an analyzing section for obtaining, by frequency analysis, Doppler data only from that component of the Doppler shifted signal which has power exceeding a predetermined blank level, a setting section for setting system conditions influencing the noise level of the Doppler shifted signal, and a control section for substantially controlling the blank level of the analyzing section in accordance with the conditions set by the setting section.

21 Claims, 4 Drawing Sheets

ULTRASONIC DIAGNOSTIC APPARATUS

BACKGROUND OF THE INVENTION

1. Field of the Invention

The present invention relates to an ultrasonic diagnostic apparatus for transmitting/receiving an ultrasonic wave to obtain Doppler shift data of the ultrasonic wave in an object to be examined, obtaining movement data in the object by performing frequency analysis of the data, and using the movement data for a display.

2. Description of the Related Art

A conventional ultrasonic diagnostic apparatus often uses an ultrasonic transducer array constituted by a plurality of ultrasonic transducer elements.

In linear electronic scan, a predetermined number of ultrasonic transducer elements selected from a plurality of ultrasonic transducer elements constituting an ultrasonic transducer array are excited as a group, and an ultrasonic beam is transmitted. These ultrasonic transducer elements constituting one group are repeatedly excited in a pulse-like manner, while simultaneously and sequentially changing the selection of the ultrasonic transducer elements of that group in units of one element, thus electronically and sequentially shifting the transmission position of an ultrasonic beam to be transmitted. In linear electronic scan, the scanning of an object to be examined with an ultrasonic beam is done by using such a sequential shift of the transmission position of the ultrasonic beam. An ultrasonic beam transmitted from the group of ultrasonic transducer elements can be focused by creating phase differences between the transmitted sound waves from respective elements. This is obtained by shifting the time of excitation of the elements depending on their lateral positions relative to the beam, i.e., beam axial positions versus beam peripheral positions. Similarly, an ultrasonic beam received by the group of ultrasonic transducer elements can be focused in effect by utilizing phase differences between the signals received by the respective elements. This is obtained by shifting the delay times applied to the signals in reception depending on the lateral positions of the receiving elements, i.e., beam axial positions versus beam peripheral positions. Such a technique of focusing an ultrasonic beam is called electronic focusing. In the above-described linear electronic scan, electronic focusing is used where needed. An ultrasonic wave reflected in an object to be examined, i.e., an ultrasonic echo, is received and converted into an electrical signal by the same ultrasonic transducers as were used for transmission. For example, a tomographic image is formed on the basis of echo data obtained by such transmission/reception of the ultrasonic beam, and is displayed on a TV (television) monitor or the like.

In sector electronic scan, a plurality of ultrasonic transducer elements constituting an ultrasonic transducer array are repeatedly excited as a group to transmit an ultrasonic beam in a pulse-like manner. The ultrasonic beam transmitted from these ultrasonic transducer elements can be steered by creating phase differences between sound waves from the respective elements. These are produced by gradually shifting the excitation timing of respective elements. (Similarly, regarding an ultrasonic beam to be received by the ultrasonic transducer elements, directivity can be provided to the reception sensitivity in effect by utilizing phase differences between the signals received by the respective elements. This is achieved by applying a different delay time to each of the receiving elements so as to align the respective reception signals.) By sequentially changing the excitation timing of each transducer element so as to sequentially steer the direction of the ultrasonic beam in units of pulses, a sectorial region in the object is scanned with the ultrasonic beam. When such sector electronic scan is to be performed, the above-mentioned electronic focusing is employed where needed. Received echo data is processed in basically the same manner as in the above-described linear electronic scan.

In addition to electronic scan such as the above-described linear and sector electron scan, mechanical scan is available as a technique of scan using an ultrasonic beam. In mechanical scan, a transducer is mounted on a scan mechanism, and an ultrasonic beam is moved by operating the scan mechanism.

An ultrasonic Doppler method is, typically, a method of obtaining data on the basis of movement of blood (blood flow) in a living body and visualizing it. The ultrasonic Doppler method is based on the Doppler effect that when an ultrasonic wave is reflected by a moving matter, the frequency of the reflected wave is shifted in proportion to the moving velocity of the matter. More specifically, an ultrasonic wave as a pulse is transmitted into a living body, and the phase or frequency of an ultrasonic echo as the reflected wave of the ultrasonic pulse is detected by using the transmission ultrasonic wave as a reference, thereby obtaining frequency shift data based on the Doppler effect obtained by the movement of a matter which reflected the ultrasonic wave, i.e., Doppler shift data. Movement data of the matter causing reflection of the echo can be obtained from the Doppler shift data. According to this ultrasonic Doppler method, for example, the directions of blood flows, the velocities of blood flows, and states of changes in blood flow at various positions in a living body can be detected by analyzing the Doppler shift data.

A conventional ultrasonic diagnostic apparatus for obtaining blood flow data from an ultrasonic echo by using such an ultrasonic Doppler method will be described below.

An ultrasonic transducer is driven by a transmitting/receiving circuit to repeatedly transmit a pulse-like ultrasonic beam a predetermined number of times in a given direction. A received ultrasonic echo is detected by a phase detector, and a frequency data signal is obtained. This frequency data signal includes a Doppler shifted signal and a clutter component as an unwanted low-frequency component. The frequency data signal is converted into a digital signal by an A/D converter (analog-to-digital) converter. The clutter component is then removed by a digital filter. The Doppler shifted signal is frequency-analyzed by a high-speed frequency analyzer such as a moving-target indicator (MTI) processor using an autocorrelation scheme or the like. Upon frequency analysis of the Doppler shifted signal, for example, a mean Doppler shift, a Doppler shift variance, and a mean level of the Doppler shifted signal are obtained. Data such as a blood flow velocity, a blood flow velocity variance, and the power of the Doppler shifted signal can be obtained on the basis of the obtained values.

By performing the above-described processing while performing, e.g., sector scan of the ultrasonic beam, two-dimensionally distributed blood flow data similar to a B-mode tomographic image obtained by sector scan can be obtained. The two-dimensional blood flow data (e.g., a two-dimensional blood flow velocity image representing the direction and velocity of the blood flow) obtained in this manner, is superposed/combined on/with a B-mode image; alternatively, an image representing changes in blood flow data over time is superposed/combined on/with an M-mode image, thus displaying an ultrasonic image including the blood flow data on a monitor.

In such a conventional ultrasonic diagnostic apparatus, a clutter component is removed from a phase-detected ultrasonic echo signal by using the digital filter so as to extract only a Doppler shifted signal of a blood flow. A power calculator for obtaining blood flow power includes a blanking circuit for blanking noise contained in the Doppler signal with a blank level corresponding to predetermined power level. Since the noise which is contained in the Doppler signal and which has power equal to or less than the blank level is blanked, noise displayed on the screen of a TV monitor can be reduced to improve the image quality.

In the blanking circuit of the conventional apparatus, the following problem is posed.

Figure 1:
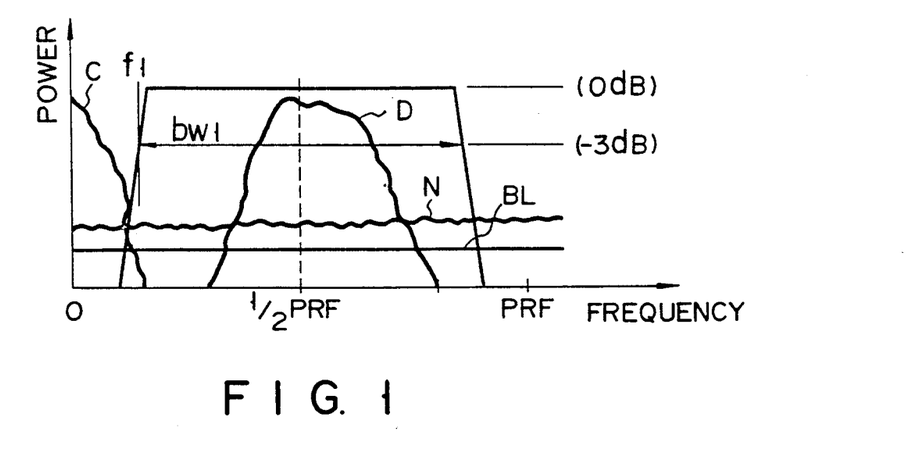
FIG. 1 is a chart for explaining blanking processing for removing a noise component of a Doppler shifted signal by using a power level as a reference in a conventional apparatus.

As shown in FIG. 1, a phase-detected ultrasonic echo signal is filtered by a digital filter having a given cutoff frequency so as to extract only a Doppler shifted signal D distributed near a frequency $\frac{1}{2}$ PRF which is $\frac{1}{2}$ a pulse rate frequency (PRF), i.e., an ultrasonic pulse repetitive frequency and to remove a clutter component C. The conventional blanking circuit has a fixed blank level BL. For this reason, if the cutoff frequency of the digital filter is set to be relatively low frequency f1, a passband bw1 of the digital filter becomes wide, and increased noise corresponding to the wide band bw1 is caused. If the power of this noise N1 exceeds the blank level BL, a noise component (N1−BL) exceeding the blank level BL appears on an ultrasonic image including blood flow data, thus degrading the image quality.

The blank level has an effect on the integral value of the energy which the noise of each frequency has after passing through a digital filter. For simplicity, the blank level and noise level shown in FIG. 1 are depicted such that they are constant for all spectra.

SUMMARY OF THE INVENTION

It is an object of the present invention to provide an ultrasonic diagnostic apparatus which can improve the image quality of an ultrasonic image by substantially changing a blank level in accordance with the magnitude of noise so as to properly blank the noise.

According to the present invention, there is provided an ultrasonic diagnostic apparatus comprising an ultrasonic transmitting/receiving section for transmitting an ultrasonic wave into an object to be examined and receiving an ultrasonic echo of the transmitted ultrasonic wave, a detecting section for detecting a frequency shift component from an ultrasonic echo signal obtained by the ultrasonic transmitting/receiving section, a filter section for removing a clutter component from a detection signal obtained by the detecting section and extracting only a required Doppler shifted signal, an analyzing section for obtaining, by frequency analysis, Doppler data only from that component of the Doppler shifted signal which has power exceeding a predetermined blank level, a setting section for setting system conditions influencing the noise level of the Doppler shifted signal, and a control section for substantially controlling the blank level of the analyzing section in accordance with the conditions set by the setting section.

According to the ultrasonic diagnostic apparatus, if a noise level is high, the blank level is substantially increased accordingly. Hence, most of noise can be removed even if a noise level is high. If a noise level is low, the blank level is decreased accordingly to prevent blanking of a Doppler signal component having a low level. Therefore, diagnosis can be performed with a displayed image effectively reflecting necessary data.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

DETAILED DESCRIPTION OF THE PREFERRED EMBODIMENT

Figure 2:
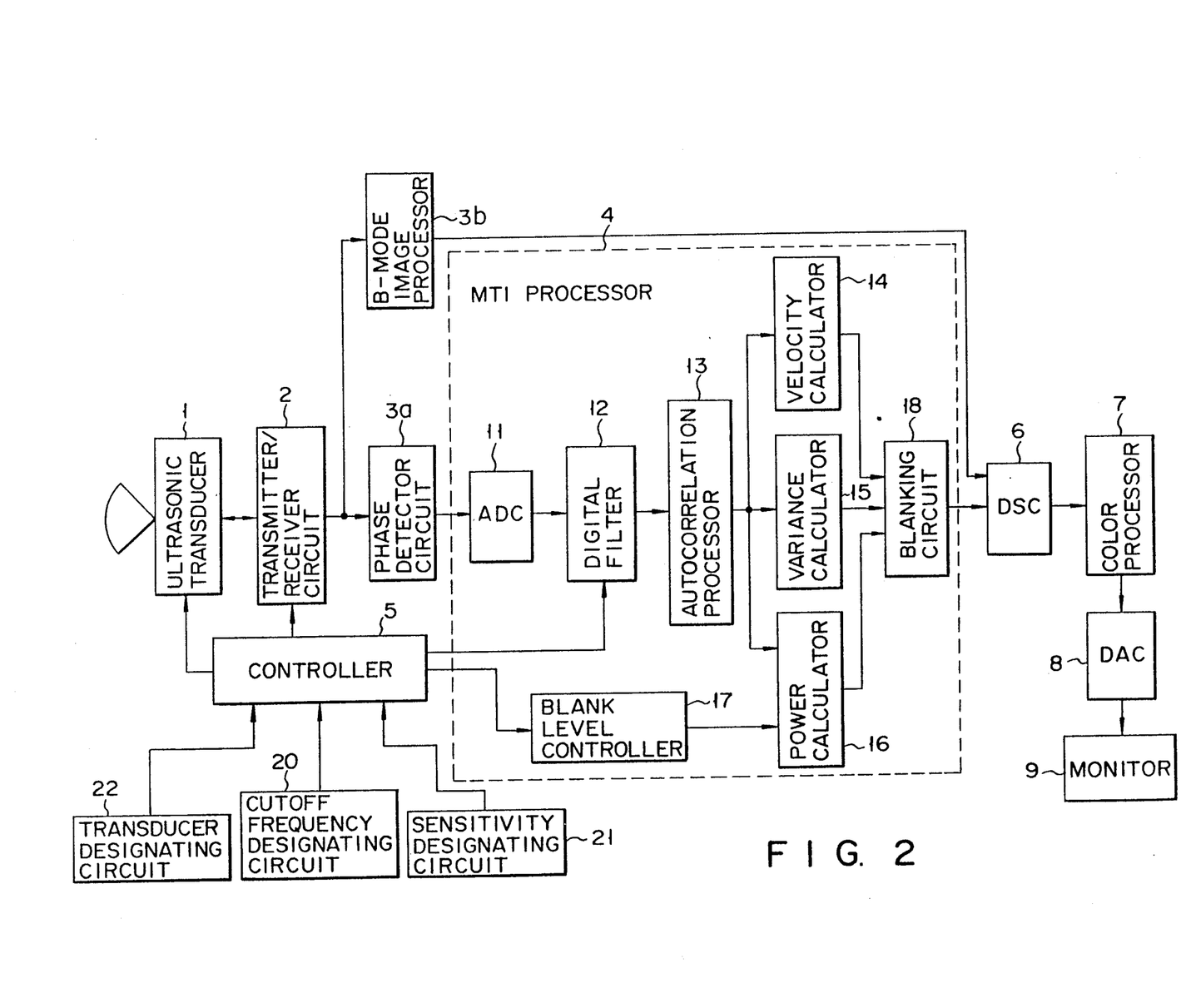
FIG. 2 is a block diagram showing an arrangement of an ultrasonic diagnostic apparatus according to the first embodiment of the present invention.

FIG. 2 shows a schematic arrangement of an ultrasonic diagnostic apparatus according to the first embodiment of the present invention.

The ultrasonic diagnostic apparatus comprises an ultrasonic transducer 1, a transmitting/receiving circuit 2, a phase detector 3a, a B-mode image processor 3b, a moving-target indicator (MTI) processor 4, a controller 5, a digital scan converter (DSC) 6, a color processor 7, a digital-to-analog converter (DAC) 8, a monitor 9, a cutoff frequency designating circuit 20, a sensitivity designating circuit 21, and a transducer designating circuit 22.

The MTI processor 4 includes an analog-to-digital converter (ADC) 11, a digital filter 12, an autocorrelation processor 13, a velocity calculator 14, a variance calculator 15, a power calculator 16, a blank level controller 17, and a blanking circuit 18.

The cutoff frequency designating circuit 20 is used to designate the cutoff frequency of a digital filter 12. The sensitivity designating circuit 21 is used to designate the sensitivity of an ultrasonic transmitting/receiving system (especially the gain of the transmitting/receiving circuit 2). The transducer designating circuit 22 is used to designate a type of ultrasonic transducer 1 to be used.

The ultrasonic transducer 1 includes various types of transducers, e.g., linear electronic scan type transducers, sector electronic scan type transducers, and the like which are classified according to scan schemes, and transducers which are classified according to the size of an ultrasonic beam to be transmitted/received. In general, an ultrasonic diagnostic apparatus can selectively use several types of transducers.

The controller 5 receives cutoff frequency data, sensitivity data, and transducer data from the cutoff frequency designating circuit 20, and the sensitivity designating circuit 21, respectively, and controls the digital filter 12, the transmitting/receiving circuit 2, and the ultrasonic transducer 1 on the basis of the received data. The noise level of a Doppler shifted signal varies depending on the cutoff frequency of the digital filter 12, the gain of the transmitting/receiving circuit 2, and the characteristics of the ultrasonic transducer 1. For this reason, the controller 5 estimates a noise level on the basis of at least one of the cutoff frequency data, the sensitivity data, and the transducer data.

The blank level controller 17 is controlled by the controller 5 and supplies a control signal for changing the blank level in accordance with the determined noise level to the power calculator 16. The power calculator 16 obtains the power level of a Doppler shifted signal on the basis of an output from the autocorrelation processor 13, and checks whether the power level exceeds the blank level corresponding to the control signal from the blank level controller 17.

The blanking circuit 18 blanks calculation results which are obtained by the velocity calculator 14 and the variance calculator 15 on the basis of a signal obtained when the power calculator 16 determines that the power level is equal to or less than the blank level.

An operation of the ultrasonic diagnostic apparatus shown in FIG. 2 will be described below.

The ultrasonic transducer 1 is driven by the transmitting/receiving circuit 2. As a result, an ultrasonic wave is transmitted as a pulse from the ultrasonic transducer 1 to an object (not shown) to be examined, i.e., a living body. When this ultrasonic pulse is reflected in the living body, an ultrasonic echo obtained. This ultrasonic echo is received by the transmitting/receiving circuit 2 through the ultrasonic transducer 1. If the ultrasonic pulse is reflected by a moving matter, e.g., blood cells in blood, in the living body, an ultrasonic echo including a Doppler shift due to a blood flow, i.e., a Doppler echo is obtained. An ultrasonic echo including the Doppler echo is received by the ultrasonic transducer 1 and the transmitting/receiving circuit 2 and is supplied as an echo signal which is an electrical signal to the phase detector 3a and the B-mode image processor 3b.

The B-mode image processor 3b envelope-detects the reception echo signal from the transmitting/receiving circuit 2 so as to form a monochrome, i.e., black and white tomographic data, and supplies it to the DSC 6.

The phase detector 3a phase-detects the reception echo signal from the transmitting/receiving circuit 2 so as to detect a frequency shift, and obtains a frequency data signal consisting of the Doppler shifted signal based on the blood flow and the clutter component. The Doppler shifted signal and the clutter component obtained by the phase detector 3a are input to the MTI processor 4. The frequency data signal output from the phase detector 3a is converted into a digital signal by the ADC 11.

The digital signal output from the ADC 11 is filtered by the digital filter 12 in accordance with the filtering characteristics with a predetermined cutoff frequency in order to remove the clutter component, thus extracting a Doppler shifted signal in a necessary frequency band. In this case, the cutoff frequency is controlled by the controller 5. The controller 5 adjusts the cutoff frequency to a frequency designated by the cutoff frequency designating circuit 20.

Figure 3A:
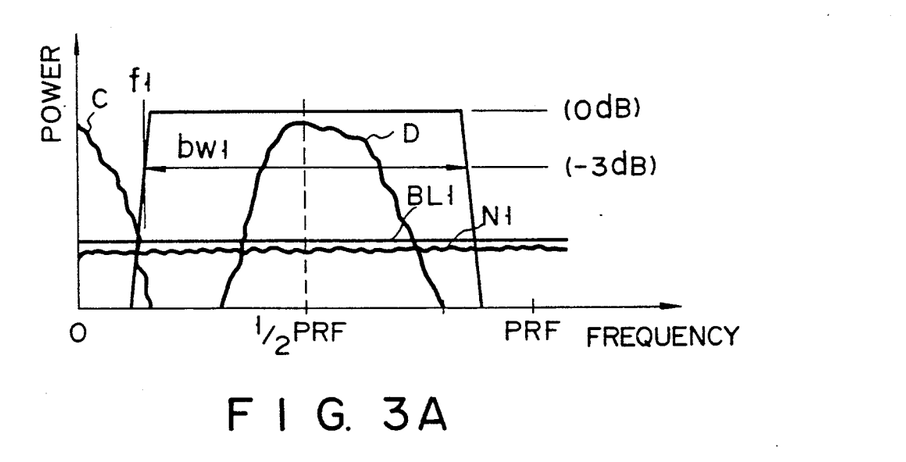
FIGS. 3A and 3B are charts for explaining blanking processing in the apparatus in FIG. 2.

Assume that the cutoff frequency is f1. In this case, as shown in FIG. 3A, the passband of the digital filter 12 becomes band bw1, and hence a clutter component C having a frequency equal to or less than the cutoff frequency is removed, thus extracting a Doppler shifted signal D. The extracted Doppler signal D is input to the autocorrelation processor 13. The autocorrelation processor 13 obtains a mean Doppler shift frequency on the basis of changes in Doppler shifted signal. The velocity calculator 14 obtains a mean velocity, i.e., a mean velocity V of the blood by using this mean frequency. The variance calculator 15 obtains a velocity variance 2. The power calculator 16 obtains power P of the Doppler shifted signal. The velocity V, the variance 2, and the power P are input from the calculators 14, 15, and 16 to the blanking circuit 18.

The controller 5 determines a noise level in accordance with designation by the cutoff frequency designating circuit 20, the sensitivity designating circuit 21, and the transducer designating circuit 22 and controls the power calculator 16 through the blank level controller 17 so as to adjust the blank level in accordance with this noise level. The power calculator 16 completely blanks Doppler data corresponding to Doppler power having a level substantially equal to or less than the blank level as noise. Therefore, blood flow data including no noise having a level equal to or less than the blank level, i.e., the velocity V, the variance 2, and the power P are supplied to the DSC 6 and are written in a frame memory in the DSC 6. B-mode image data from the B-mode image processor 3b is also written in the frame memory in the DSC 6, and the blood flow data is superposed on the B-mode image data. In the DSC 6, the image data written in the frame memory in accordance with an ultrasonic scan scheme is read out in accordance with a standard TV (television) scan scheme so as to convert an ultrasonic scan format into a TV scan format. The image data converted for a TV scan is then converted into color data by the color processor 7. This color data has a color and a luminance according to the blood flow data, i.e., the velocity V, the variance 2, and the power P. The data is then converted into an analog video signal by the DAC 8 and is displayed on the monitor 9 as a B-mode image on which the Doppler data is superposed.

Assume that a relatively low cutoff frequency is designated by the cutoff frequency designating circuit 20. In this case, if the cutoff frequency is f1, the passband of the digital filter 12 is band bw1, as shown in FIG. 3A. In this case, a relatively large noise component corresponding to the band bw1 is superposed on the Doppler signal D and is input to the autocorrelation processor 13. The controller 5 determines on the basis of data of a cutoff frequency designated by the cutoff frequency designating circuit 20 that a frequency data signal output from the digital filter 12 includes a noise component having a relatively high noise level N1. The controller 5 supplies a control signal for obtaining a blank level BL1 corresponding to the noise level N1 to the blank level controller 17. The blank level controller 17 controls the power calculator 16 so as to perform processing in accordance with the blank level BL1.

Figure 3B:
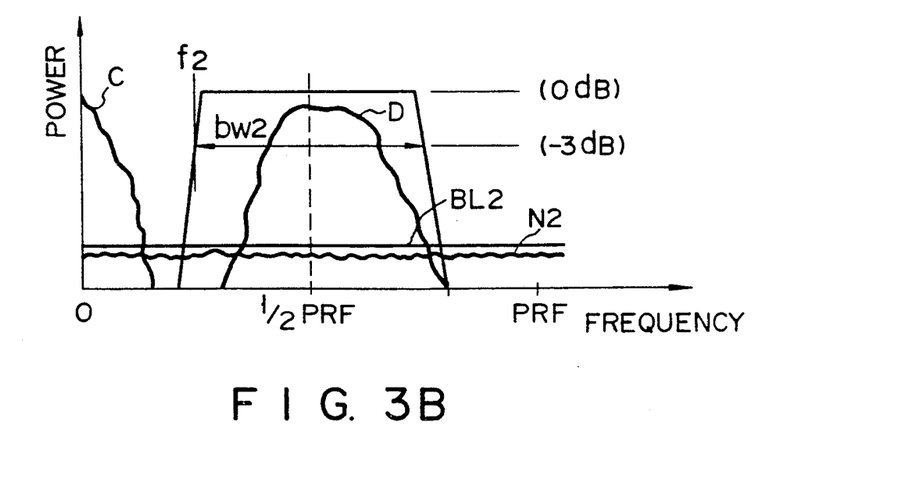

In contrast to this, as shown in FIG. 3B, if a relatively high cutoff frequency f2 is designated, a passband bw2 becomes relatively narrow, and a noise level N2 becomes low. The controller 5 then controls the blank level controller 17 to obtain a low blank level BL2 corresponding to the noise level N2 by using the power calculator 16. As is apparent from FIG. 3B, the noise N2 having a level substantially equal to or less than the blank level BL2 is completely blanked.

In this manner, a blank level is variably controlled in accordance with a noise level which is changed depending on the cutoff frequency of the digital filter 12. Therefore, when a low cutoff frequency is designated, although the passband of the digital filter 12 is broadened and the noise level is increased, the blank level B is increased in accordance with this increase. Hence, most noise can be removed. If the cutoff frequency of the digital filter 12 is high, although the passband of the digital filter 12 is narrowed and the noise level becomes lower than that obtained when the cutoff frequency is low, the blank level is decreased in accordance with this decrease. Hence, Doppler shifted signal components having low levels are used for a display without being blanked, and good image quality can be obtained.

Similarly, when sensitivity data is input from the sensitivity designating circuit 21 to the controller 5, the controller 5 controls the sensitivity of the transmitting-/receiving circuit 2 in accordance with the sensitivity data. As a result, the gain of the transmitting/receiving circuit 2 is changed. With this change in gain, the level of a noise component included in a Doppler signal is changed. The controller 5 determines a noise level on the basis of the sensitivity data and controls the blank level controller 17 in accordance with this noise level, thereby obtaining a blank level corresponding to the noise level.

When a type of ultrasonic transducer 1 is designated by the transducer designating circuit 22, the ultrasonic transducer 1 is controlled by the controller 5 in accordance with the designated type. Since the noise level is also changed depending on the type of ultrasonic transducer 1, the controller 5 determines a noise level in accordance with data of the type of ultrasonic transducer 1 designated by the transducer designating circuit 22. The controller 5 then adjusts a blank level through the blank level controller 17 in accordance with the noise level.

Since control of a blank level corresponding to designation of the cutoff frequency designating circuit 20, the sensitivity designating circuit 21, and the transducer designating circuit 22 is performed in a combined manner, an optimal blank level can always be obtained.

Figure 4:
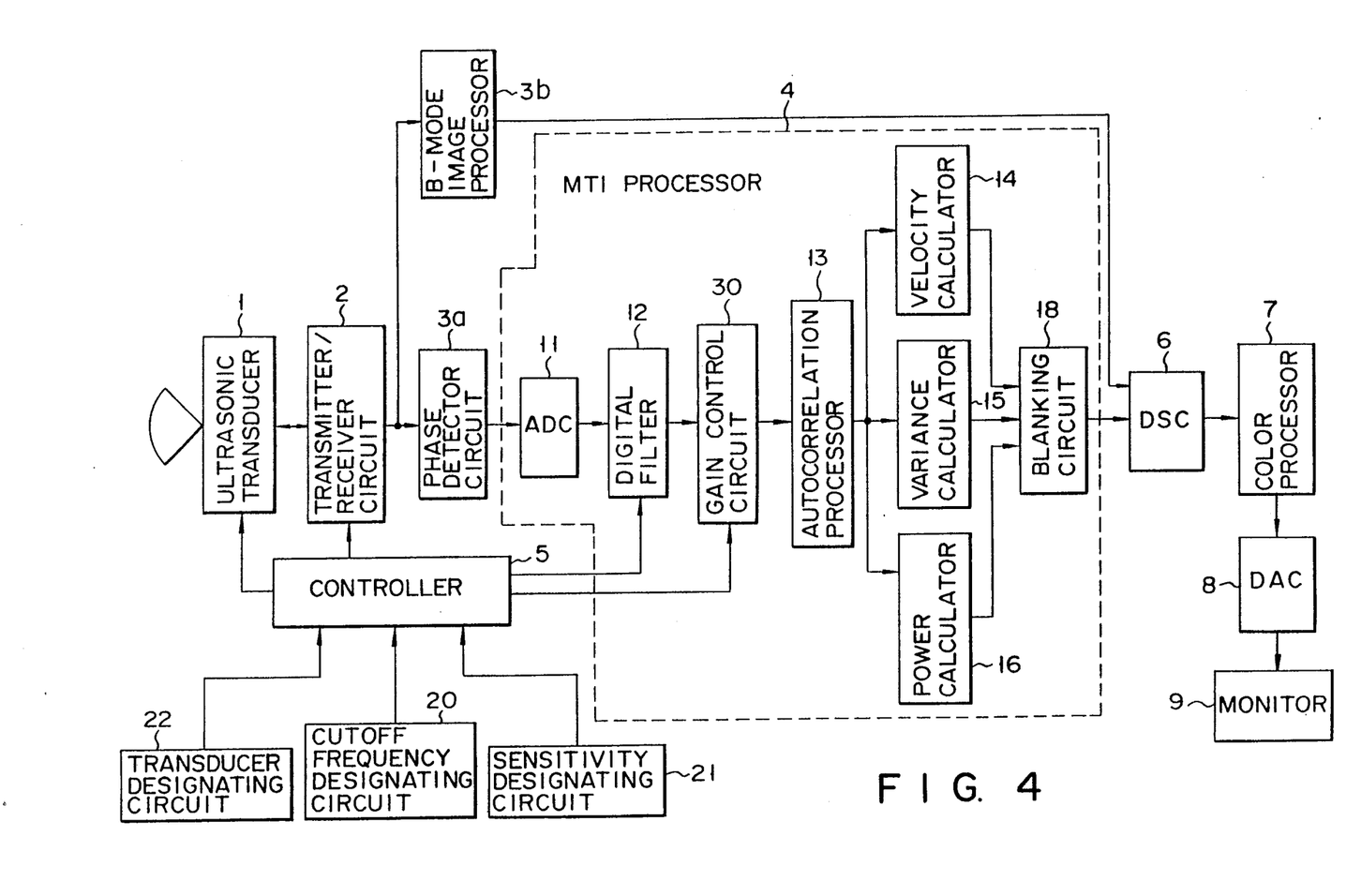
FIG. 4 is a block diagram showing an arrangement of an ultrasonic diagnostic apparatus according to the second embodiment of the present invention.

FIG. 4 shows a schematic arrangement of an ultrasonic diagnostic apparatus according to the second embodiment of the present invention.

The apparatus shown in FIG. 4 is designed to control the magnitude of a frequency data signal output from a digital filter 12 while the blank level is fixed instead of controlling the blank level. For this purpose, the apparatus in FIG. 4 includes a gain control circuit 30 in place of the blank control circuit 17 shown in FIG. 2. The gain control circuit 30 is arranged between the digital filter 12 and an autocorrelation processor 13 and is constituted by a multiplier for multiplying an output from the digital filter 12 by a predetermined value.

In the gain control circuit 30, a multiplier factor with respect to an output from the digital filter 12 is controlled by a controller 5. With this control, if the gain is increased, the blank level is equivalently decreased in relation to the gain and vice versa.

Figure 5:
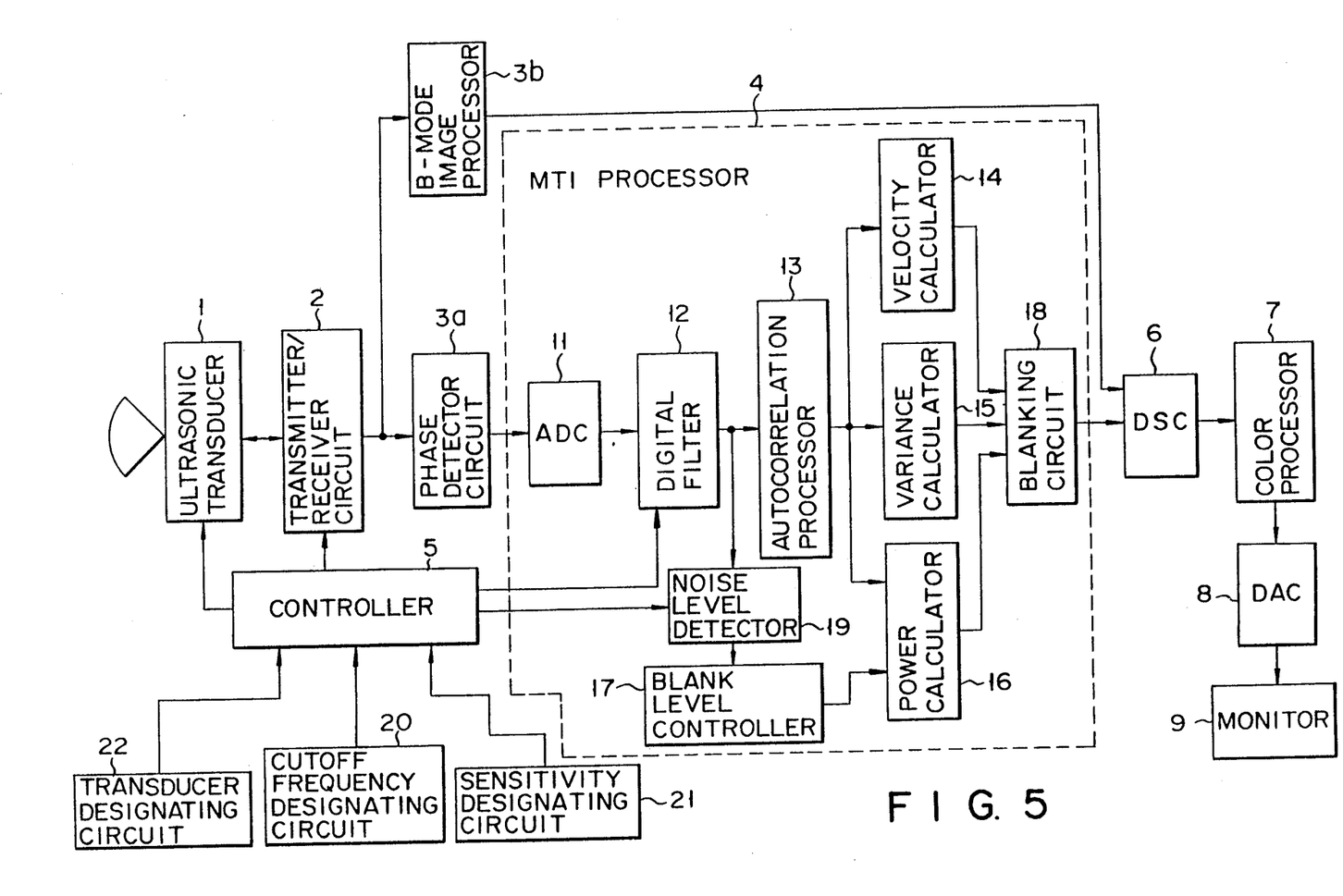
FIG. 5 is a block diagram showing an arrangement of an ultrasonic diagnostic apparatus according to the third embodiment of the present invention.

FIG. 5 shows a schematic arrangement of an ultrasonic diagnostic apparatus according to the third embodiment of the present invention.

The apparatus shown in FIG. 5 is designed to detect a noise level and control the blank level in accordance with the detected noise level instead of controlling the blank level in accordance with cutoff frequency data, sensitivity data, and transducer data. For this purpose, the apparatus in FIG. 5 includes a noise level detector 19 for detecting a noise level upon reception of an output from a digital filter 12 in addition to the arrangement shown in FIG. 2. The noise level detector 19 is controlled by the controller 5. In this case, a blank level controller 17 is not controlled by the controller 5 but is controlled by an output from the noise level detector 19.

The noise level detector 19 incorporates an autocorrelation processor, a velocity calculator, a variance calculator, and a power calculator substantially similar to the autocorrelation processor 13, the velocity calculator 14, the variance calculator 15, and the power calculator 16. The noise level detector 19 analyzes the characteristics of data input from the digital filter 12 by using cutoff frequency data, sensitivity data, and transducer data input from the controller 5 so as to check whether the data is noise, thus detecting a noise level. In this determination processing, if data of a portion to be diagnosed is independently input, the detection precision can be further increased by supplying it from the controller 5 to the level detector 19.

The noise level detector may be designed such that it detects and stores a noise level obtained when the system does not transmit ultrasonic waves. In addition, the blank level may be varied with time in accordance with the depth of the region where the ultrasonic echo information is reflected.

The present invention is not limited to the above-described embodiments. In the embodiments, relatively low and high frequencies are exemplified as cutoff frequencies. However, the present invention is not limited to this but other frequencies may be used.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasonic diagnostic apparatus comprising:
    ultrasonic transmitting/receiving means for transmitting an ultrasonic wave into an object to be examined and receiving an ultrasonic echo of the transmitted ultrasonic wave;
    detecting means for detecting a frequency shift component from an ultrasonic echo signal obtained by said ultrasonic transmitting/receiving means;
    filter means for removing a clutter component from a detection signal obtained by said detecting means and extracting only a required Doppler shifted signal;

analyzing means for frequency analyzing the Doppler shifted signal output from said filter means to obtain predetermined Doppler data only when a power of the Doppler shifted signal exceeds a predetermined blank level;

setting means for setting system conditions influencing the noise level of the Doppler shifted signal; and control means for substantially controlling the blank level of said analyzing means in accordance with the conditions set by said setting means.

2. An apparatus according to claim 1, wherein the system conditions include an ultrasonic transmitting/receiving condition of said ultrasonic transmitting/receiving means.

3. An apparatus according to claim 2, wherein said ultrasonic transmitting/receiving means is means capable of selectively using a plurality of types of ultrasonic transducers, and said setting means is means for designating the ultrasonic transmitting/receiving condition including a selecting condition of said ultrasonic transducers.

4. An apparatus according to claim 1 wherein the system conditions include a filtering frequency condition of said filter means.

5. An apparatus according to claim 4, wherein said filter means is means capable of variably setting a cutoff frequency, and said setting means is means for designating the filtering frequency condition including a setting condition of the cutoff frequency.

6. An apparatus according to 4, wherein said ultrasonic transmitting/receiving means includes gain adjusting means for adjusting a reception gain of said ultrasonic transmitting/receiving means, and said setting means is means for designating the sensitivity condition including a control condition of said gain adjusting means.

7. An apparatus according to claim 1, wherein the system conditions include a sensitivity condition of said ultrasonic transmitting/receiving means.

8. An apparatus according to claim 1, wherein said analyzing means includes autocorrelation processing means for frequency-analyzing the Doppler shifted signal, velocity calculating means for calculating a velocity on the basis of a processing result obtained by said autocorrelation processing means, variance calculating means for calculating a velocity variance on the basis of the processing result obtained by said autocorrelation calculating means, and power calculating means for obtaining power of a Doppler shifted signal on the basis of the processing result obtained by said autocorrelation processing means and neglecting a Doppler shifted signal having a level not more than the blank level, and said control means is means for changing the blank level by controlling said power calculating means.

9. An apparatus according to claim 1, wherein said analyzing means includes gain adjusting means for adjusting a gain of an output from said filter means, and said control means is means for changing a level of a Doppler shifted signal in relation to the blank level by controlling said gain adjusting means.

10. An apparatus according to claim 1, wherein said ultrasonic transmitting/receiving means includes means for transmitting/receiving an ultrasonic wave in accordance with a predetermined ultrasonic scan mode, ultrasonic scan image forming means for forming ultrasonic scan image data on the basis of an ultrasonic echo signal obtained by said ultrasonic transmitting/receiving means, and synthesizing means for forming composite image data by combining the Doppler data obtained by said analyzing means with the ultrasonic scan image data formed by said ultrasonic image forming means.

11. An apparatus according to claim 1, wherein said predetermined Doppler data is a velocity of a moving object causing a Doppler shift, a variance of the velocity, and a power of the Doppler shifted signal, and said predetermined Doppler data are overlappingly displayed on a tomographic image obtained by detecting the ultrasonic echo.

12. An ultrasonic diagnostic apparatus comprising:

ultrasonic transmitting/receiving means for transmitting an ultrasonic wave into an object to be examined and receiving an ultrasonic echo of the transmitted ultrasonic wave;

detecting means for detecting a frequency shift component from an ultrasonic echo signal obtained by said ultrasonic transmitting/receiving means;

filter means for removing a clutter component from a detection signal obtained by said detecting means and extracting only a required Doppler shifted signal;

analyzing means for frequency analyzing the Doppler shifted signal output from said filter means to obtain predetermined Doppler data only when a power of the Doppler shifted signal exceeds a predetermined blank level;

noise level detecting means for detecting a noise level of the Doppler shifted signal extracted by said filter means; and control means for substantially controlling a blank level of said analyzing means in according with the noise level detected by said noise level detecting means.

13. An apparatus according to claim 12, wherein said noise level detecting means includes means for discriminating a noise level on the basis of an ultrasonic transmitting/receiving condition of said ultrasonic transmitting/receiving means.

14. An apparatus according to claim 12, wherein said noise level detecting means includes means for discriminating a noise level on the basis of a filtering frequency condition of said filter means.

15. An apparatus according to claim 12, wherein said noise level detecting means includes means for discriminating a noise level on the basis of a sensitivity condition of said ultrasonic transmitting/receiving means.

16. An apparatus according to claim 12, wherein said noise level detecting means includes autocorrelation processing means for frequency-analyzing the Doppler shifted signal, velocity calculating means for calculating a velocity on the basis of a processing result obtained by said autocorrelation processing means, variance calculating means for calculating a velocity variance on the basis of the processing result obtained by said autocorrelation calculating means, power calculating means for obtaining power of a Doppler shifted signal on the basis of the processing result obtained by said autocorrelation processing means, and level determining means for discriminating a noise level on the basis of the velocity, the variance, and the power obtained by said respective calculating means.

17. An apparatus according to claim 12, wherein said noise level detecting means includes autocorrelation processing means for frequency-analyzing the Doppler shifted signal, velocity calculating means for calculating a velocity on the basis of a processing result obtained by said autocorrelation processing means, variance calculating means for calculating a velocity variance on the basis of the processing result obtained by said autocorrelation calculating means, power calculating means for obtaining power of a Doppler shifted signal on the basis of the processing result obtained by said autocorrelation processing means, portion designating means for designating a portion to be diagnosed, and level determining means for discriminating a noise level on the basis of data of the velocity, the variance, the power, and the portion obtained by said velocity calculating means, said variance calculating means, said power calculating means, and said portion designating means.

18. An apparatus according to claim 12, wherein said analyzing means includes autocorrelation processing means for frequency-analyzing the Doppler shift signal, velocity calculating means for calculating a velocity on the basis of a processing result obtained by said autocorrelation processing means, variance calculating means for calculating a velocity variance on the basis of the processing result obtained by said autocorrelation calculating means, and power calculating means for obtaining power of a Doppler shifted signal on the basis of the processing result obtained by said autocorrelation processing means and neglecting a Doppler shifted signal having a level not more than the blank level, and said control mean is means for changing the blank level by controlling said power calculating means.

19. An apparatus according to claim 12, wherein said analyzing means includes gain adjusting means for adjusting a gain of an output from said filter means, and said control means is means for changing a level of a Doppler shifted signal in relation to the blank level by controlling said gain adjusting means.

20. An apparatus according to claim 12, wherein said ultrasonic transmitting/receiving means includes means for transmitting/receiving an ultrasonic wave in accordance with a predetermined ultrasonic scan mode, ultrasonic scan image forming means for forming ultrasonic scan image data on the basis of an ultrasonic echo signal obtained by said ultrasonic transmitting/receiving means, and synthesizing means for forming composite image data by combining the Doppler data obtained by said analyzing means with the ultrasonic scan image data formed by said ultrasonic scan image forming means.

21. An apparatus according to claim 12, wherein said predetermined Doppler data is a velocity of a moving object causing a Doppler shift, a variance of the velocity, and a power of the Doppler shifted signal, and said predetermined Doppler data are overlapping displayed on a tomographic image obtained by detecting the ultrasonic echo.

* * * * *